United States Patent
Stiles

(10) Patent No.: US 6,838,440 B2
(45) Date of Patent: Jan. 4, 2005

(54) KOLLA2-DESICCATED AVIAN STERNAL CARTILAGE POWDER

(75) Inventor: Terri Lynn Stiles, Laguna Beach, CA (US)

(73) Assignee: Collagen Nutraceuticals, Inc., Lake Forest, CA (US)

( * ) Notice: Subject to any disclaimer, the term of this patent is extended or adjusted under 35 U.S.C. 154(b) by 472 days.

(21) Appl. No.: 09/768,141

(22) Filed: Jan. 24, 2001

(65) Prior Publication Data

US 2002/0137688 A1 Sep. 26, 2002

(51) Int. Cl.[7] ............................................... A61K 38/39
(52) U.S. Cl. ....................................................... 514/21
(58) Field of Search ........................ 514/2, 21; 530/536, 530/412; 435/212, 273, 68; 426/32

(56) References Cited

U.S. PATENT DOCUMENTS

| | | | | |
|---|---|---|---|---|
| 4,389,487 A | * | 6/1983 | Ries ............................. 435/273 |
| 5,073,373 A | * | 12/1991 | O'Leary et al. ............. 424/422 |
| 6,025,327 A | * | 2/2000 | Alkayali ........................ 514/2 |

* cited by examiner

Primary Examiner—Robert A. Wax
Assistant Examiner—Robert B. Mondesi
(74) Attorney, Agent, or Firm—Craig McLaughlin; Levin & O'Connor

(57) ABSTRACT

Kolla2 powder compositions, method of preparing the compositions and use of the compositions in treating arthritic joint cartilage diseases. The compositions are orally administered to human in need of cartilage cell repair in a daily dietary supplement dosage of between about 2,400 mg and 3,600 mg.

6 Claims, 1 Drawing Sheet

KOLLA2-DESICCATED AVIAN STERNAL CARTILAGE POWDER

FIELD OF THE INVENTION

The present invention provides a composition useful as a dietary food supplement for treating arthritis by oral consumption by mammals. Said composition comprising Kolla2 extracted from desiccated avian sternal cartilage collagen type II powder, a method of manufacturing Kolla2 powder and its use for arthritis as a therapeutic agent and nutritional food supplements.

BACKGROUND OF THE INVENTION

One of every 3 American over the age of 60 suffers from osteoarthritis. It is a natural wear and tear of joint cartilage. As we age, the body's ability to make the protein Type II Collagen slows down. This is the protein needed to maintain and rebuild cartilage tissue. Collagen is a complex structural protein, which provides strength and flexibility to all connective tissues. Collagen is a major component of muscles, tendons, cartilage, ligaments, joints and blood vessels. There are four main types of collagen: II, III, IV, and I. Type I and III are primarily found in skin, tendon and bone. In contrast, collagen type II is found predominately in articulator cartilage. Collagen is an unusual protein, in that the proportion of glycine residues is nearly one-third which is unusually high. Proline is also present to a much greater extent in collagen that in most other proteins. Moreover, collagen contains two amino acids, 4-hydroxyprolineand 5-hydroxylysine, that are found in very few other proteins. The amino acid sequence of collagen is remarkably regular, nearly every third amino acid is glycine. In addition, the sequence of glycine-proline-hydroxyproline recurs frequently. In contrast, globular proteins rarely exhibit regularities in their amino acid sequences (Stryer, L., *Biochemistry*, Third Edition, W. H. Freeman and Co., New York, 1988, pp.262).

In 1986, collagen was sold for the first time in the United States for use as a food Supplement. Collagen (a mixture of Types I and Type III) was extracted from calf skin tissue, and prepared in powder form for use as a dietary supplement.

In 1987, the composition was sold compressed into 1,000 mg. tablets which comprised collagen powder and 10 mg. Vitamin C.

U.S. Pat. No. 4,804,745 to Koepff et al. Discloses agents containing collagen peptides produced by enzymatic hydrolysis for the treatment of degenerative joint diseases. These peptides can be obtained from animal skin, animal bones and other sufficiently purified connective tissue and have average molecular weights of between 30 and 45 kilodaltons.

U.S. Pat. No. 5,399,347 to Trentham et al. And Trentham et al. (*Science* 261:1727–1729, 1993) disclose the effective treatment of rheumatoid arthritis (RA) with water-soluble whole chick collagen type II or biologically active peptides derived therefrom. The mechanism by which the effect is believed to occur is via oral tolerization.

U.S. Pat. No. 5,364,845 to Henderson discloses a therapeutic composition and method for the protection, treatment and repair of connective tissue in mammals. This composition comprises glucosamine, chondroitin sulfate and manganese ascorbate. U.S. Pat. No. 5,587,363 to Henderson discloses a therapeutic composition and method for the protection, treatment and repair of connective tissue in mammals which includes aminosugars and glycosaminoglycans.

U.S. Pat. No. 6,025,327 to Alkayali discloses a therapeutic composition and method for the protection, treatment and repair of joint cartilage in mammals. This composition comprises hydrolyzed collagen type II water—soluble, denatured collagen type II obtained from chicken sternal cartilage.

The demand for compositions suitable for prevention of degenerative joint disease will surpass the demand of arthritis treatment. The present invention addressed this need.

SUMMARY OF THE INVENTION

The art of the present invention is Kolla2 —desiccated avian sternal cartilage collagen type II powder, the kolla2 powder having an average molecular weight of between about 45,000 and 65,000 daltons. Preferably, the kolla2 has an average molecular weight of about 50,000 daltons. In one aspect of this preferred art, the kolla2 is obtained from desiccated young avian sternal cartilage. Preferably, the avian sternal cartilage is collected from 4–8 week old chicks. The kolla2 is partially water-soluble and the composition comprises 20% to 30% mucopolysaccharide (carbohydrate) and 65% to 70% Collagen type II (protein) and the content of 1% to 3% lipids is part of the kolla2 composition. The present invention also provides a method of helping cartilage formation in Human with a connective tissue disorder, degenerative joint diseases, comprising orally administering to the individual an effective of daily cartilage-inducing amount of kolla2 powder.

The degenerative joint diseases include cartilage injuries, joint defects, rheumatoid arthritis, osteoarthritis, vascular disease, polychondritis, and connective tissue disorder. Preferably, the effective daily dosage amount is between about 600 mg and 10,000 mg. More preferably, the effective daily dosage amount is between about 1,200 and 7,200 mg. Most preferably, the effective daily dosage amount is between 2,400 and 3,600 mg. Another embodiment of the invention is a method of providing kolla2 as a preventative nutritional supplement, comprising orally administering to an individual a daily dosage of kolla2 having an average molecular weight of between about 45,000 and 65,000 daltons.

Stile another embodiment of the invention is a method of preparing kolla2 powder, comprising the following steps: cutting fresh 4 to 8 weeks young chicken sternal cartilage to within not less than about 2 mm of the bone; grinding cartilage into ground mesh, suspending ground cartilage in an aqueous solution; sterilizing said cartilage, filtering the ground cartilage, defatting the ground cartilage, drying the ground cartilage, milling the dried cartilage to form desiccated sternal avian cartilage powder—kolla2.

The method may further comprise the step of deep freezing the cartilage after cutting step. Preferably, the aqueous solution is water. Advantageously, grinding the deep frozen cartilage into ground mesh. In one aspect of this preferred embodiment, the sterilization process step comprises a temperature control at a minimum of 95° C. for a minimum of 30 minutes. Preferably, the drying step comprises a temperature control at a minimum 95° C. for a minimum of 6 hours. Preferably, the milling into powder and the bulk density at 20° C. is approximately about 600 g/l.

DETAILED DESCRIPTION OF THE PREFERRED ARTS

Figure 1:
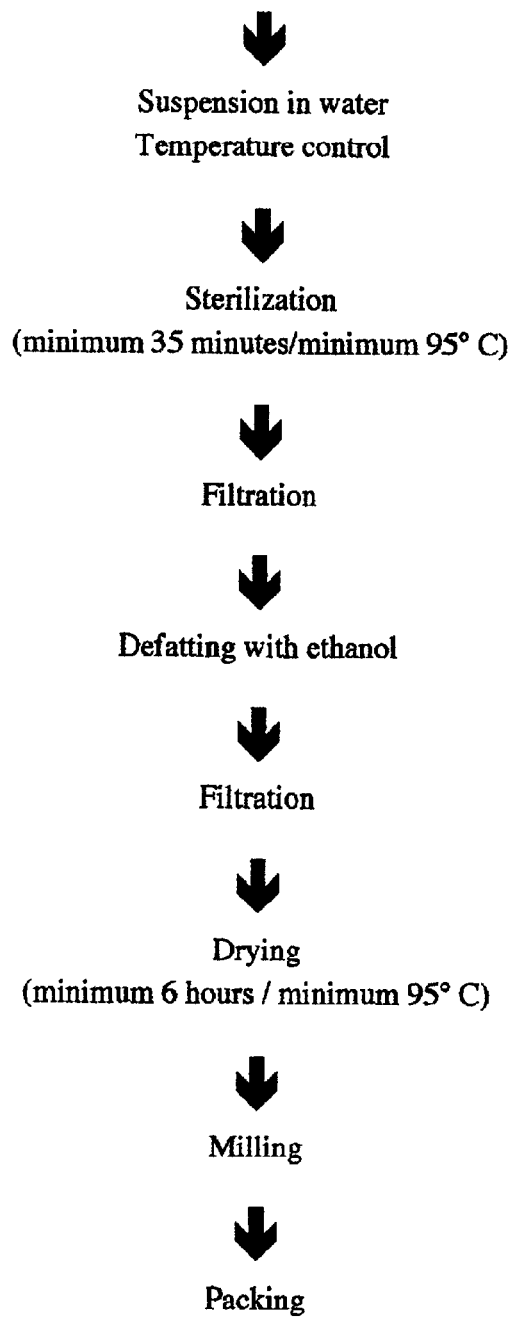
FIG. 1 is a schematic diagram of the process for preparing and the manufacturing of kolla2 dissipated sternal avian cartilage powder of the invention.

The present invention provides a kolla2 desiccated avian sternal cartilage denatured collagen II protein composition, method for preparing the composition and use of the composition in the treatment and repair of cartilage defects, and the prevention of arthritis diseases. The method involves cutting fresh sternal cartilage from 4 to 8 weeks avian carcasses and removing all meat, blood and bone therefrom. The sternal cartilage is cut leaving a space of about two and a half millimeters from the bone so as to not remove any bone fragments. This is essential to the purity of the final product because it avoids contamination of collagen type II protein with types III and I found in bone. The fresh sternal cartilage is then promptly deep-frozen and the remained of the chicken carcass is discarded. It is important the sternal cartilage, cut so no bone is included, that is used for preparing the kolla2 powder, The sternal cartilage is processed according to good manufacturing practice (GMP). Other contemplated sources of collagen type II are mammalian (i.e. bovine and porcine) and shark fins.

The production of kolla2 desiccated avian sternal cartilage in powdered form is shown in FIG. 1. Ground deep-frozen cartilage is suspended in an aqueous solution, preferably water and sterilized at temperature control at about 95° C. for a minimum of 30 minuets. The water is removed by filtration and cartilage mesh is treated with ethanol to remove excess fat, filtration and drying the sternal cartilage at a temperature between about 95° C. for a minimum of 6 hours. The dried sternal cartilage is milled to a fine mesh powdered, preferably bulk density at 20° C. is approximately about 600 g/l. The kolla2 powder is packed in a 50 kg, drum with a plastic bag liner. The powder is partially water-soluble.

The average molecular weight of the final powder is between 45,00 and 65,000 daltons, preferably 50,000 daltons. The final powder product is 20% to 30% mucopolysaccharides, particularly chondroitin sulfate and glucosamine sulfate. The product has 375 calories per 100 grams, contains 65% collagen type II protein (13.1 total nitrogen), and 20% carbohydrate and 2% lipids. Kolla2 powder is ready to be utilized after the human body's superior natural enzyme break down the amino acid chain into the precise genetic code for joint cartilage repair. The natural lipids found in kolla2 together with collagen II protein and carbohydrates constitute the chief structural components of joint cartilage cell. The unique amino acid composition and molecular weight of the kolla2 differs substantially from typical collagen proteins and is shown in Table 1. Tryptophan and hydroxylysine amino acids are absent and hydroxyproline is low. The molecular weight and amino acid composition and the natural lipids which is essential to promote optimal assimilation of the peptides.

When kolla2 is taken orally as a daily dietary supplement by an individual with a degenerative joint disorder, kolla2 helps fabricate cartilage and considerably improves the joint disorder. "Oral" administration includes oral, enteral or intragastric administration. The kolla2 of the invention can be used to trat, for instance, degenerative joint disease (i.e. rheumatoid arthritis), osteoarthritis, cartilage injuries, joint defects, connective tissue disorder, polychondritis, vascular disease, silicone poisoning due to leakage in breast implants, autoimmune diseases involving connective tissue autoantibodies (i.e. rheumatoid arthritis), progressive myopia, menier's disease and any other connective tissue disorder which would benefit from increased synthesis of cartilage.

For oral administration as a nutritional dietary supplement, therapeutic or prophylactic agent, the kolla2 of the invention may be provided as a dispersible powder or granule, tablet, hard or soft capsule, emulsion, aqueous or oil suspension, syrup or elixir. Compositions intended for oral use may be prepared in accordance with any method known in the art for the manufacturing of nutritional supplement compositions and such compositions may contain one or more of the following components: preservatives, sweeteners, flavoring agents and coloring agents. The flavoring agents and sweetening will enhance the palatability of the preparation. Tablets containing kolla2 in admixture with non-toxic pharmaceutically acceptable excipients suitable for tablet manufacture are acceptable. Such excipients include inert diluents such as calcium carbonate, sodium carbonate, lactose, calcium phosphate or sodium phosphate, granulating and disintegrating agents, such as corn starch or alginic acid, binding agents such as starch, gelatin or acacia; and lubricating agents such as magnesium stearate, stearic acid or talc, Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed. The use of enteric coating is also contemplated. Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the kolla2 powder of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweeting agents, such as those set forth above, and flavoring agents may be added to provide a palatable oral preparation. These compositions may be preserved by an added antioxidant such as ascorbic acid. Dispersible powders and granules of the invention suitable for preparation of an aqueous suspension by the addition of water provide the active ingredient in admixture with a dispersing or wetting agent, a suspending agent, and one or more preservatives. Additional excipients, for example, sweetening, flavoring and coloring agents may also be present. Syrups and elixirs may be formulated with sweetening agents, such as glycerol, sorbitol or sucrose. Such formulations may also contain a demulcent, a preservative, a flavoring agent and/or a coloring agent. The kolla2 powder may be mixed with other ingestible forms and consumed in solid, semi-solid solution, suspension or emulsion form. It may also be mixed in conjunction or alternatively with pharmaceutically carriers, flavor enhancers, water, suspending agents and emulsifying agents. In a preferred embodiment, the kolla2 powder is mixed with a citrus juice such as orange, grapefruit or tangerine due to the promotion of connective tissue formation by ascorbic acid. In a preferred essence, the kolla2 may also be formulated in admixture with ascorbic acid.

For use as a nutritional dietary supplement, prophylactic or therapeutic agent. Kolla2 is orally administered in a daily dosage of between about 600 mg capsule and 10,000 mg. More preferably, it is administered in a daily dosage of between about 3,600-mg and 7,200 mg. Most preferably, it is administered in a daily dosage of between about 2,400 and 3,600 mg. per day. The kolla2 may by formulated into tablets that range from 600 mg. to 1,000 mg. per tablet, In a preferred embodiment, the kolla2 powder is formulated into 600-mg tablets and 4–6 tablets are taken daily. In another preferred embodiment, the tablets are taken on an empty stomach with a beverage containing vitamin C. In another preferred embodiment, the kolla2 powder is mixed with water or a citrus juice prior to ingestion. The preparations described above can be taken indefinitely by individuals affected by connective tissue disorders or by healthy individuals as a preventative agent. The above detailed description of the invention is set forth solely to assist in understanding the invention. It is to be understood that variations of the invention, including all equivalents now known or later developed are to be considered as falling within the scope of the invention, which is limited only by the following claims.

What is claimed is:

1. A method of preparing cartilage-derived material comprising collagen type II in powder form, comprising the steps:

(a) cutting avian sternal cartilage to within not less than 2 mm of the sternum and removing the cut sternal cartilage from the sternum;

(b) freezing the cut sternal cartilage into frozen cartilage;

(c) grinding the frozen cartilage into ground-cartilage;

(d) suspending the ground cartilage in an aqueous solution;

(e) sterilizing the ground cartilage;

(f) filtering the sterilized ground cartilage;

(g) defatting the ground cartilage;

(h) filtering the defatted ground cartilage;

(i) drying the ground cartilage; and (j) milling the dried ground cartilage into powder form.

2. The method of claim 1 wherein the aqueous solution is water.

3. The method of claim 1 wherein the sterilizing step includes heating the ground cartilage to at least 95° C. for at least 30 minutes.

4. The method of claim 1 wherein the defatting step includes treating the ground cartilage with ethanol.

5. The method of claim 1, wherein the drying step includes heating the ground cartilage to at least 95° C. for at least 6 hours.

6. The method of claim 1, wherein the dried ground cartilage is milled into a powder form having a size between about 80 mesh to 200 mesh.

* * * * *